United States Patent [19]
Postell et al.

[11] Patent Number: 5,456,665
[45] Date of Patent: Oct. 10, 1995

[54] INTRA-AORTIC BALLOON CATHETER

[75] Inventors: Susan J. Postell, Reading; Jeffrey P. Lewis, Wyomissing, both of Pa.

[73] Assignee: Arrow International Investment Corp., Wilmington, Del.

[21] Appl. No.: 206,317

[22] Filed: Mar. 4, 1994

[51] Int. Cl.⁶ .................................................. A61M 29/00
[52] U.S. Cl. ............................ 604/96; 604/282; 606/194
[58] Field of Search .................................. 604/96, 95, 280, 604/282, 264; 606/191–194

[56] References Cited

U.S. PATENT DOCUMENTS

| | | | |
|---|---|---|---|
| 5,176,660 | 1/1993 | Truckai | 604/282 |
| 5,176,661 | 1/1993 | Evard et al. | 604/282 |
| 5,180,376 | 1/1993 | Fischell | 604/282 |
| 5,279,596 | 1/1994 | Castaneda et al. | 604/282 |

OTHER PUBLICATIONS

"Ready the instant it's in your hands", RediFurl DL Product Brochure (1987).
Kontron Instruments 9.5F/10.5F Double Lumen Cardiothane Pre–Wrapped Percutaneous IAB Product Brochure (Dec. 1992).
Mansfield Cardiac Assist, New! 9.5 Fr Sidewinder DL IAB Product Brochure (1990).

*Primary Examiner*—John D. Yasko
*Attorney, Agent, or Firm*—Amster, Rothstein & Ebenstein

[57] ABSTRACT

An improved intra-aortic balloon catheter of the present invention with a kink-resistant outer tube formed of a helically wound metal coil overlaid with a plastic covering which maintains the patency of the air passageway, and a central tub, forming a secondary lumen, formed of a strong resilient, flexible, kink-resistant material, such as a super elastic metal alloy.

13 Claims, 4 Drawing Sheets

INTRA-AORTIC BALLOON CATHETER

BACKGROUND OF THE INVENTION

Intra-aortic balloon catheters are used in patients with left heart failure to augment the pumping action of the heart. The catheters, approximately 1 meter long, have an inflatable and deflatable balloon at the distal end. The catheter is typically inserted into the femoral artery, and moved up the descending thoracic aorta until the distal tip of the balloon is positioned just below or distal to the left subclavian artery. An air passageway for inflating and deflating the balloon extends through the catheter and is connected at its proximal end to an external pump. The patient's ECG may be used to produce balloon inflation in synchronous counter pulsation to the patient's heart beat.

Intra-aortic balloon therapy increases coronary perfusion, decreases the workload of the left ventricle, and allows healing of the injured myocardium. Ideally, the balloon should be inflating just as the aortic valve closes and deflating just prior to the onset of systole. When properly coordinated, the inflation of the balloon raises the patient's diastolic pressure, increasing the oxygen supply to the myocardium; and balloon deflation just prior to the onset of systole lowers the patient's diastolic pressure, reducing myocardial oxygen consumption.

Intra-aortic balloon catheters may also have a central passageway or lumen which can be used to measure aortic pressure. In this dual lumen construction, the central lumen may also be used to accommodate a guide wire to facilitate placement of the catheter, or may be used to infuse fluids, or to do blood sampling.

Typical dual lumen intra-aortic balloon catheters have an outer, flexible, plastic tube and a central tube therethrough formed of plastic tubing, stainless steel tubing, or wire coil embedded in plastic tubing. Polyurethane is used to form the balloon. Problems associated with current intra-aortic balloon catheter constructions are kinking of the outer tube, kinking of the central tube, and restriction of a blood flow to the legs caused by the position and size of the catheter in the artery.

It is an object of the present invention to provide an improved intra-aortic balloon catheter with a kink-free outer tube leading to reduced kinking of the air passage lumen.

It is another object of the present invention to provide an improved intra-aortic balloon catheter with a strong flexible kink-resistant central tube formed of a strong resilient, flexible, kink-resistant metal alloy tube.

It is another object of the present invention to provide an improved intra-aortic balloon catheter with an air passage lumen of increased cross section for greater air flow.

It is another object of the present invention to provide an improved intra-aortic balloon catheter of reduced outer diameter to decrease its resistance to blood flow in the descending aorta.

SUMMARY OF THE INVENTION

The improved intra-aortic balloon catheter of the present invention has a kink-resistant outer tube formed of a helically wound metal coil overlaid with a plastic covering which maintains the patency of the air passageway. In addition, the central tube, forming the central lumen may be formed of a resilient, flexible, kink resistant material, such as a super elastic metal alloy.

Use of a super elastic metal alloy to make the central tube permits the tube to be constructed with a thinner wall thickness than the prior art, plastic, stainless steel, or composite central tubes. The smaller central tube permits a greater cross-sectional flow area through the air passageway lumen and/or use of a smaller diameter outer tube. Reducing the outer diameter of the outer tube reduces the catheter's resistance to blood flow, and permits use of a smaller introducer sheath, further reducing resistance to blood flow, or increasing circulation to the legs.

DESCRIPTION OF THE INVENTION

Figures 1, 1A:
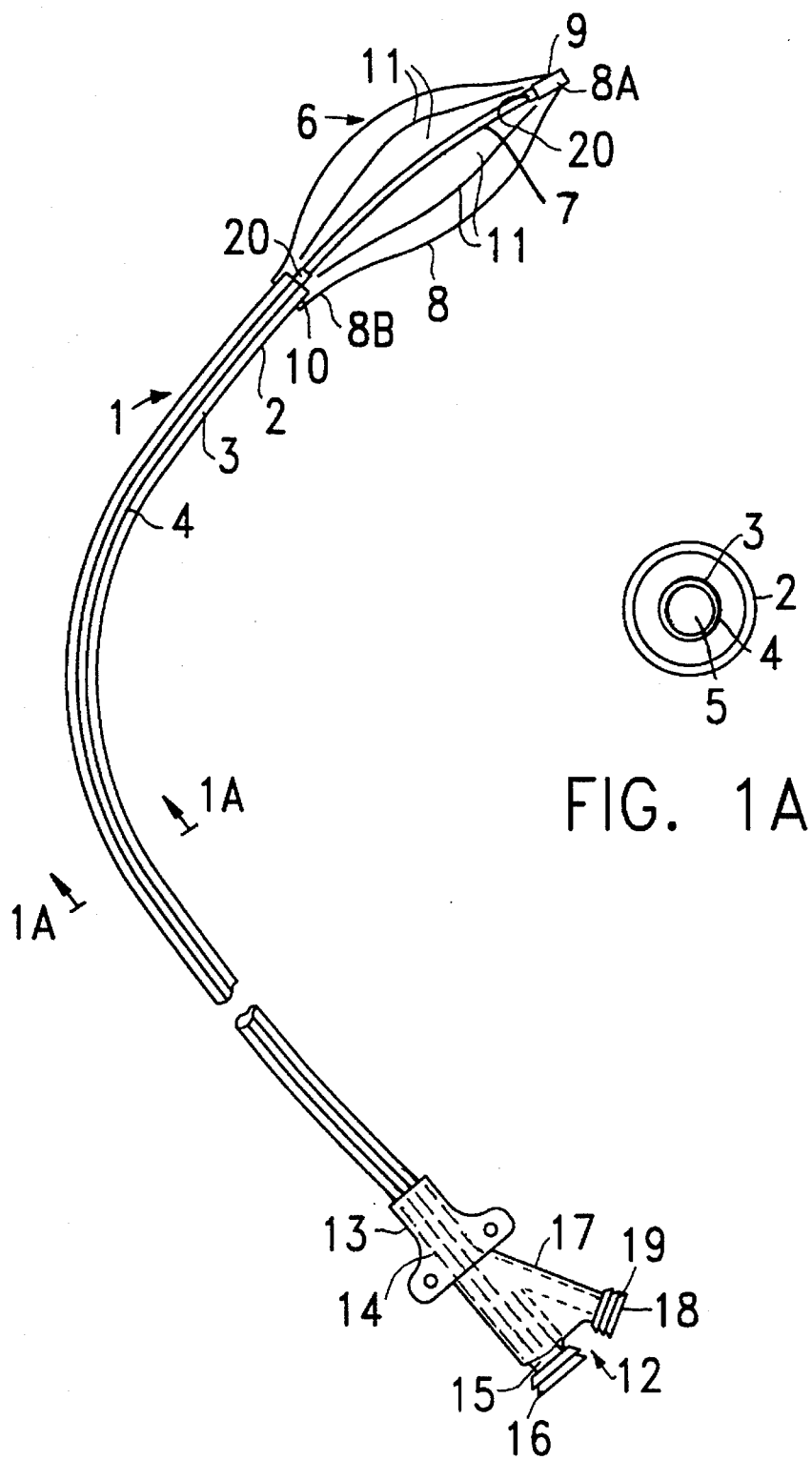
FIG. 1 is a plane view of a prior art intra-aortic balloon catheter.
FIG. 1A is a transverse cross sectional view of the prior art catheter of FIG. 1 taken along lines 1A—1A.

The general structure of an intra-aortic balloon catheter is best described in relation to FIGS. 1 and 1A which illustrate a dual-lumen prior art intra-aortic balloon catheter. The catheter, shown generally at 1, is constructed of a clear plastic outer tube, 2, forming an air passageway lumen, 3; and another clear plastic central tube, 4, disposed within outer tube, 2, and creating a central passageway or lumen, 5, as may best be seen in FIG. 1A.

A balloon is disposed at the distal end of the catheter, shown generally at 6. The distal portion, 7, of the central tube, 4, extends beyond the distal end, 10, of outer tube, 2. The distal end of the balloon, 8A, is attached to a tip, 9, formed on the distal end, 7, of central tube, 4. The proximal end of the balloon, 8B, is attached to the distal end, 10, of the outer tube. The distal portion, 7, of the central tube supports the balloon. It must have sufficient strength to prevent inversion of the balloon as it inflates and deflates under aortic pressure but flexible enough to be safely inserted through an introducer sheath, moved through the arterial tree, and maintained in the thoracic aorta.

The balloon is formed of a nonthrombogenic flexible material, such as polyurethane, and may have folds, 11, formed as a result of wrapping the balloon about the central tube to ease insertion of the catheter. Radio-opaque bands, 20, at the distal end of the catheter aid in positioning the balloon in the descending aorta.

Inflation and deflation of the balloon is accomplished through the air passageway lumen. The central passageway or lumen can accommodate a guide wire for placement or repositioning of the catheter. When the guide wire is not disposed in the central lumen, the central lumen may be used for measuring blood pressure in the descending aorta. This pressure measurement may be used to coordinate the inflation and deflation of the balloon with the pumping of the heart, however, use of the patient's ECG is preferred. Additionally, the central lumen may be used to infuse liquids into the descending aorta, or to sample blood.

At the proximal end of the catheter, shown generally at 12, a hub 13 is formed on the proximal end 14 of outer tube 2. The central passageway or lumen, 5, extends through the hub, and a connector 16 is provided at the proximal end 15 (or exit) of the central passageway or lumen, 5. Measurement of aortic pressure and blood sampling may be done through proximal end, 15, of the central passageway.

The proximal end, 18, of the air passageway lumen, 3, exits through a side arm, 17, of the hub, on which is provided a connector, 19. The proximal end, 18, of the air passageway lumen may be connected to an intra-aortic balloon pump.

Figures 2, 2A:
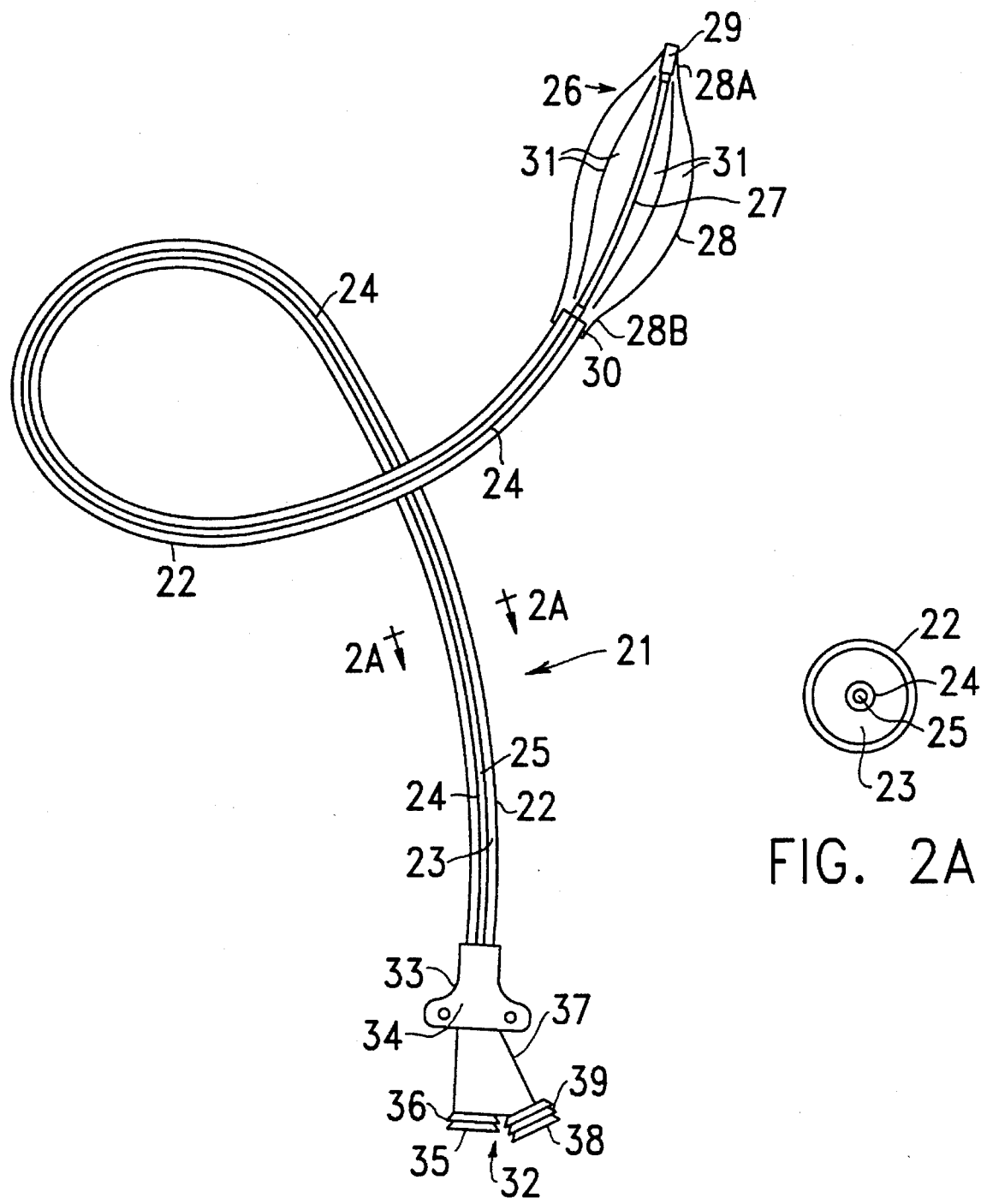
FIG. 2 is a plane view of an improved intra-aortic balloon catheter of the present invention with a kink resistant inner tube.
FIG. 2A is a transverse cross-section of the catheter of FIG. 2, taken along lines 2A—2A.

One embodiment of the improved intra-aortic balloon catheter of the present invention is illustrated in FIGS. 2 and 2A. The improved catheter shown generally at 21 comprises an outer tube, 22, of a flexible plastic material such as polyurethane and a central tube, 24, of kink-resistant metal alloy, defining an air passageway lumen, 23, therebetween. Numbered parts 25–39 correspond to parts 5–19 of FIGS. 1 and 1A, and reference may be had to the description of parts 5–19 to describe parts 25 to 39 of the embodiment of the invention shown in FIGS. 2 and 2A.

Use of the kink-resistant metal alloy such as Nitinol, manufactured and sold by Raychem Corp., permits the central tube, 24, to be constructed with a smaller wall thickness and hence a much smaller outer diameter than conventional central tubes made of plastic material or stainless steel. Thus, the cross-sectional area of the air passageway lumen, 23, may be increased and/or the outer diameter of the outer tube, 22, may be decreased, improving blood flow around the catheter to the legs.

In use, intra-aortic balloon catheters are generally inserted through an introducer sheath into the femoral artery and threaded up through the descending aorta until the balloon tip is disposed just distal to the left subclavian artery. Insertion of the catheter through the sheath, and the process of placement of the catheter, can lead to kinking or permanent damage of the central tube of the catheter. Permanent deformation of the distal portion of the central tube may cause the balloon to improperly inflate and deflate causing excessive wear or rupture of the balloon, or abrasion of the vessel wall.

Kinking of the catheter is often not apparent until the catheter has been fully placed and balloon inflation and deflation attempted. Kinking of the central lumen may not become apparent until the wire guide has been removed. Inability to infuse through the central lumen or to measure blood pressure through the central lumen may require that the catheter be removed from the body and another inserted. Hence it is highly desirable that the central lumen remains kink free and undeformed.

Though Nitinol is the preferred material for tube 24, the tube may alternatively be formed of a similar strong, flexible, resilient material. These properties in the material produce a flexible, non-kinking central tube making the catheter easy to insert. In addition, the resilience of the central tube prevents deformation or kinking of the tube once inserted. Lastly, the strength of the central tube prevents balloon inversion in on an otherwise flexible resilient central tube.

When formed of Nitinol, the central tube, 24, may have a wall thickness of 2.0 to 3.5 mils, compared to the 10 mil thick plastic central tubes of the current intra-aortic balloon catheters. The strong, thin-walled Nitinol central tubes are, however, more flexible, more resilient, and more kink-resistant than the prior art stainless steel central tubes. The reduction in wall thickness of 6.5 to 7 mils can be used to effectively increase the cross-sectional of the air passageway lumen and/or to decrease the outer diameter of the outer tube, 22. Specifically, reduction in the central tube wall thickness to 2 to 3.5 mils can lead to a reduction in catheter size or outer diameter or outer tube from 8½ French, to 7 to 7½ French, or less, permitting the use of a reduced size introducer sheath. Reduction in outer diameter of outer tube, 22, and the ability to use a smaller sheath reduces the blockage of blood flow to the legs making the catheter safer to use for longer periods of time.

The balloon, 28, is attached at its proximal end, 28B, by conventional means such as a solvent based adhesive, to the distal end, 30, of the tube, 22, and at its distal end, 28A, to the distal end, 29, of tube, 24. The proximal end, 35, of the central lumen extends through the hub and a connector, 36, may optionally be provided for connecting the proximal end of the central lumen to tubing connecting the lumen with a pressure measuring device, or source of injectate. The proximal end, 35, of the central lumen extends generally straight back through the hub to make that lumen readily available as a guide wire lumen for placement of the catheter. The proximal end, 38, of the air passageway lumen may extend through a sidearm, 37, of the hub as shown, such that the proximal end of the air passageway lumen exits at a point displaced from the exit of the central lumen. A connector, 39, is provided for the proximal end of the air passageway lumen to connect it with a source for pumped gas, preferably helium. When the central tube, 24, is formed of a metal alloy, it is identifiable under X-ray or fluoroscope, and radio-opaque bands may not be needed at the distal end of the catheter for locating the balloon within the body of the patient.

Figure 3:
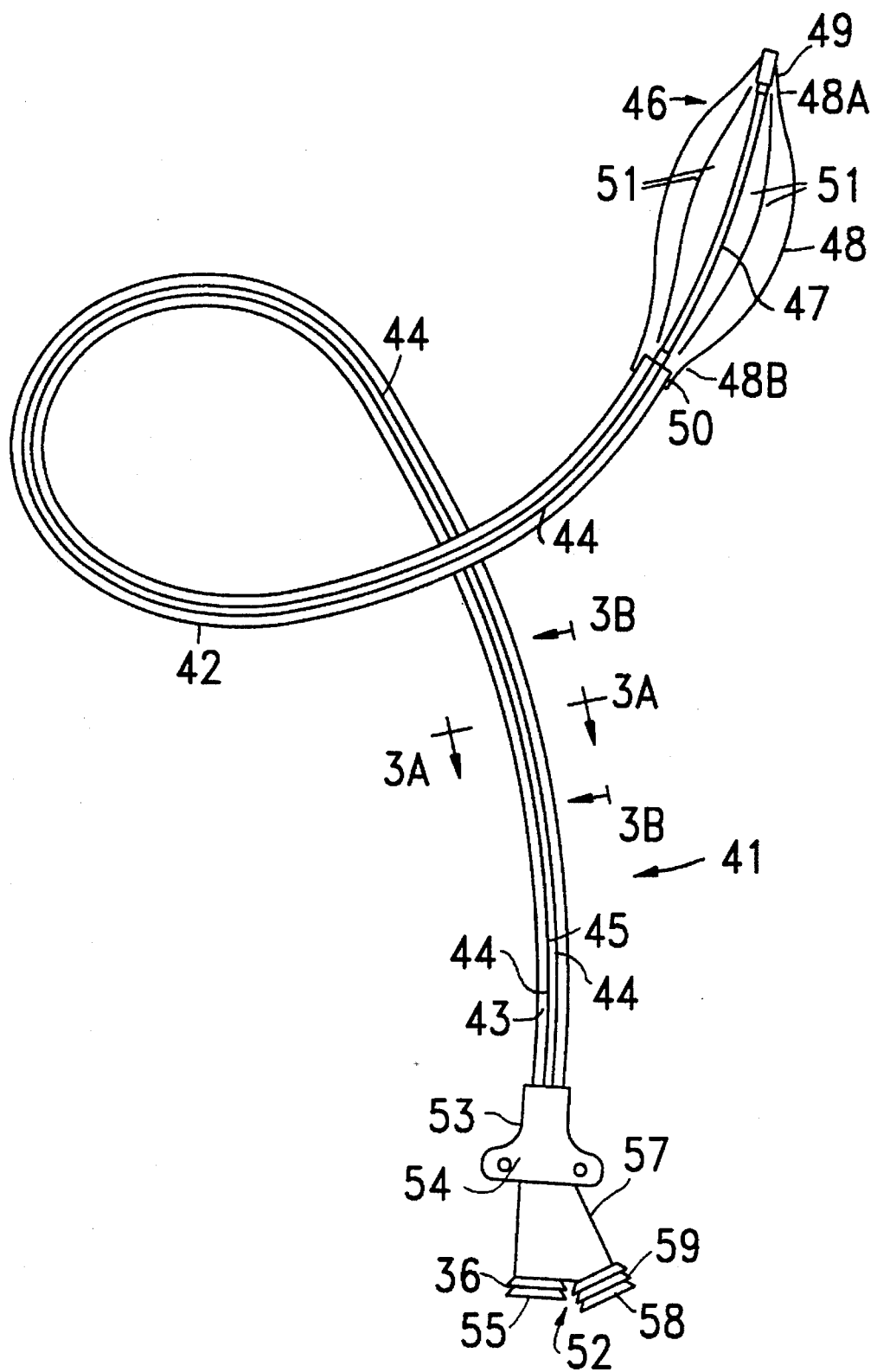
FIG. 3 is a plane view of an improved intra-aortic catheter of the present invention with a kink resistant outer tube.
Figure 3B:
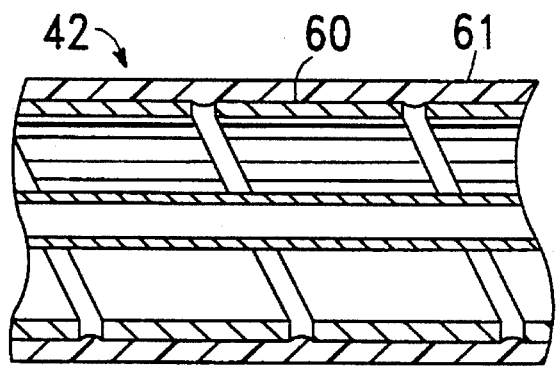
FIG. 3B is a longitudinal cross section of a catheter of FIG. 3 taken along lines 3B—3B.
Figure 3A:
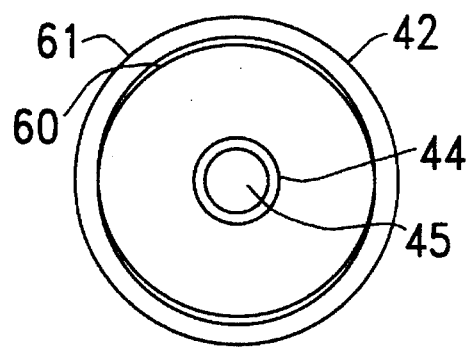
FIG. 3A is a transverse cross sectional of the catheter of FIG. 3 taken along lines 3A—3A.
Figure 3C:
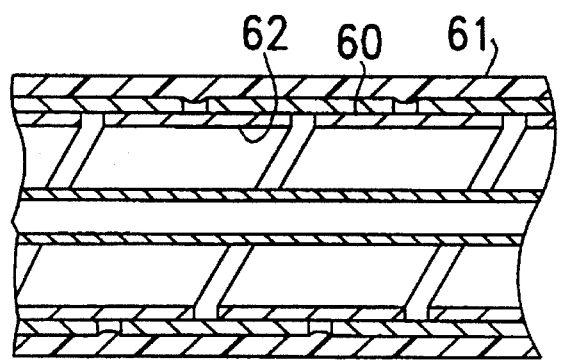
FIG. 3C is a longitudinal cross-section of an alternative embodiment of the catheter construction of FIG. 3 and 3A.

Another embodiment of the improved intra-aortic balloon catheter of the present invention is illustrated in FIGS. 3 to 3C. The improved catheter shown generally at 41 comprises kink resistant outer tube, 42, formed of a metal coil within a plastic covering. Description of the remaining elements, 43–59, may be had by reference to the description of corresponding elements, 23–39, of FIG. 2 and 2A.

Insertion of the catheter through the sheath, and the process of placement of the catheter, can lead to kinking or permanent damage of the outer tube of the catheter. Inability to inflate and deflate the balloon through the air passageway lumen, requires that the entire catheter be removed from the body and another inserted. Deformation of the air passageway lumen can also cause the balloon to inflate and deflate improperly causing excessive wear or rupture of the balloon, or abrasion of the vessel wall. Hence it is highly desirable that the air passageway lumen remain kink free. The entire outer tube, but at least the proximal portion, may be formed of this kink-resistant construction, as the greatest kinking forces are imposed as the outer tube passes through the sheath.

The construction of outer tube, 42, may best be seen in FIGS. 3A through 3C. The tube, 42, may be formed of a central helical metal coil, 60, which lies within a plastic covering, 61. This non-buckling kink-free construction, used to form a catheter insertion sheath, is described in U.S. Pat. No. 5,180,376 and co-pending application Ser. No. 07/965, 961. The metal coil is typically fabricated from a flat stainless steel wire or an equivalent springy metal. The thickness of the metal is typically between 1 and 5 mils and the width of the wire is typically between 5 to 50 times the wire thickness. This ratio of wire width to thickness is an important consideration in thin walled structure that does not collapse in use. Greater width-to-thickness ratios are required as wire thickness is decreased. Wire of thickness 2.5 to 3.5 mil requires a width-to-thickness ratio of 3 to 20, wire of thickness 1.5 mils to 2.49 mils requires a width-to-thickness ratio of 5 to 50, while wire of thickness 0.75 mils to 1.49 mils requires a width-to-thickness ratio of 12 to 80.

The flat wire is typically wound on a mandrel in a manner similar to the way that spring wire guides are made at the present time. The plastic covering, 61, is typically made from polyethylene, polyurethane, PVC or a similar plastic material. One method of forming the covering, 61, so that it fits tightly around the helical coil, 60, would be by sliding the coil, 60, through a tube of plastic and then heat shrinking the plastic onto the helical coil, 60. Further, optionally, the interior surface of the coil may be coated with plastic. Another method would be to dip coat the coil, 60, into a liquid plastic material that hardens onto the coil.

In the alternative construction shown in FIG. 3C, the helical coil may be constructed of two separate metal coils, one inside the other, wound in opposite directions to improve the strength of the tube. As shown in FIG. 3C, the outer tube, 42, comprises a central metal coil, 62, and an outer helical metal coil, 60, which lie within the plastic covering, 61. Additionally, the interior surface of the central metal coil may be coated with plastic.

Use of an outer tube with metal coil only, or of a central metal or metal alloy tube alone, might require additional means to identify the ends of the balloon by X-ray or fluoroscopy. However, use of an outer tube, 42, and inner tube, 24, requires no additional radio-opaque bands at the distal end of the catheter for locating the balloon within the body of the patient.

Various other modifications, adaptations, and alternative designs are, of course, possible in light of the above teachings. Therefore, it should be understood at this time that within the scope of the appended claims, the invention may be practiced otherwise then as specifically described herein.

What is claimed is:

1. In a balloon catheter including an outer tube with proximal and distal ends, and a central tube having proximal and distal ends and being disposed within said outer tube and extending beyond said distal end of said outer tube, and a balloon with a proximal end attached to said distal end of said outer tube and a distal end attached to said distal end of said central tube, the improvement comprising at least a proximal portion of said outer tube comprising a kink-resistant construction of a flat wire metal coil consisting of a multiplicity of turns having some separation between adjacent turns of said metal coil, the interior surface of said coil forming an air passageway lumen of the catheter, a plastic covering fitted onto and in contact with the exterior surface of said coil, said plastic covering extending into the space between adjacent turns of said metal coil, said central tube being formed of a resilient, kink-resistant super elastic metal alloy.

2. The balloon catheter of claim 1 wherein the resilient, kink-resistant material of the central tube is Nitinol.

3. The balloon catheter of claim 1 wherein the flat wire coil is stainless steel.

4. The balloon catheter of claim 1 wherein the flat wire of metal coil has a thickness between 2.5 and 3.5 mils and a width-to-thickness ratio of between 3 and 20.

5. The balloon catheter of claim 1 wherein the flat wire of the metal coil has a thickness between 1.5 and 2.49 mils and a width-to-thickness ratio between 5 and 50.

6. The balloon catheter of claim 1 wherein the flat wire of the metal coil has a thickness between 0.75 and 1.49 mils and a width-to-thickness ratio between 12 and 80.

7. The balloon catheter of claim 1 wherein the metal coil has a space between adjacent turns that is less than the width of a single turn of the coil.

8. The balloon catheter of claim 1 wherein the interior surface of the metal coil is coated with plastic.

9. The balloon catheter of claim 1 wherein the flat wire coil comprises an inner helical metal coil covered by an outer helical metal coil which is covered by said plastic covering.

10. A balloon catheter including an outer tube with proximal and distal ends, and a central tube disposed within the outer tube and extending beyond the distal end of the outer tube, and a balloon with proximal end attached to the distal end of the outer tube, and distal end attached to the distal end of the central tube, the improvement comprising the central tube comprising a resilient, kink-resistant material.

11. The balloon catheter of claim 10 wherein the resilient, kink-resistant material is a super elastic metal alloy.

12. The balloon catheter of claim 11 wherein the resilient, kink-resistant material is Nitinol.

13. In a balloon catheter including an outer tube with proximal and distal ends, and a central tube disposed within the outer tube and extending beyond the distal end of the outer tube, and a balloon with proximal end attached to the distal end of the outer tube, and distal end attached to the distal end of the central tube, the improvement characterized by the central tube comprising a resilient, kink-resistant material, and at least the proximal portion of the outer tube comprising a kink-resistant construction of a flat wire metal coil consisting of a multiplicity of turns having some separation between adjacent turns of the metal coil, the interior surface of said coil forming the aid passageway lumen of the catheter, a plastic covering fitted onto and in contact with the exterior surface of said coil, said plastic covering extending into the space between adjacent turns of the metal coil.

* * * * *

(12) REEXAMINATION CERTIFICATE (4363rd)
United States Patent
Postell et al.

(10) Number: US 5,456,665 C1
(45) Certificate Issued: May 22, 2001

(54) INTRA-AORTIC BALLOON CATHETER

(75) Inventors: Susan J. Postell, Reading; Jeffrey P. Lewis, Wyomissing, both of PA (US)

(73) Assignee: Arrow International Investment Corp., Wilmington, DE (US)

Reexamination Request:
No. 90/005,022, Jun. 22, 1998

Reexamination Certificate for:
Patent No.: 5,456,665
Issued: Oct. 10, 1995
Appl. No.: 08/206,317
Filed: Mar. 4, 1994

(51) Int. Cl.⁷ .................................................. A61M 29/00
(52) U.S. Cl. .................... 604/103.09; 604/523; 604/526; 606/194
(58) Field of Search ............................. 604/96, 523, 524, 604/525, 526, 530, 532, 103.09; 606/191–194

(56) References Cited

U.S. PATENT DOCUMENTS 5,397,306    3/1995   Nobuyoshi et al. .

FOREIGN PATENT DOCUMENTS 5-31194    *  2/1993  (JP) .
WO9317750    9/1993  (WO) .

* cited by examiner

*Primary Examiner*—Richard K. Seidel

(57) ABSTRACT

An improved intra-aortic balloon catheter of the present invention with a kink-resistant outer tube formed of a helically wound metal coil overlaid with a plastic covering which maintains the patency of the air passageway, and a central tube, forming a secondary lumen, formed of a strong resilient, flexible, kink-resistant material, such as a super elastic metal alloy.

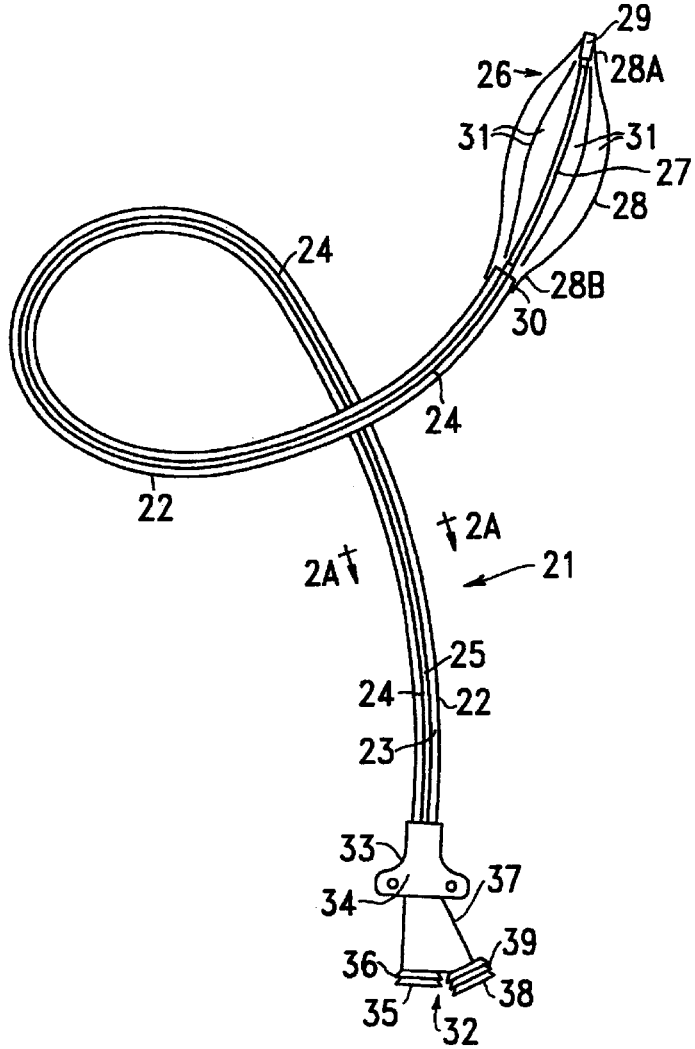

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–9 and 13 is confirmed.

Claims 10, 11 and 12 are cancelled.

\* \* \* \* \*